US011448673B2

(12) United States Patent
Lyden et al.

(10) Patent No.: US 11,448,673 B2
(45) Date of Patent: Sep. 20, 2022

(54) REDUCTION OF NOISE IN IMPEDANCE MEASUREMENT CIRCUITS

(71) Applicant: Analog Devices International Unlimited Company, Limerick (IE)

(72) Inventors: Colin G. Lyden, Baltimore (IE); Thomas J. Tansley, Andover, MA (US); Oliver J. Brennan, Oakland, CA (US)

(73) Assignee: Analog Devices International Unlimited Company, Limerick (IE)

( * ) Notice: Subject to any disclaimer, the term of this patent is extended or adjusted under 35 U.S.C. 154(b) by 29 days.

(21) Appl. No.: 17/088,098

(22) Filed: Nov. 3, 2020

(65) Prior Publication Data

US 2021/0373056 A1    Dec. 2, 2021

Related U.S. Application Data

(60) Provisional application No. 63/032,913, filed on Jun. 1, 2020.

(51) Int. Cl.
*G01R 27/16*    (2006.01)
*A61B 5/053*    (2021.01)

(52) U.S. Cl.
CPC .............. *G01R 27/16* (2013.01); *A61B 5/053* (2013.01)

(58) Field of Classification Search
CPC .... G01R 27/16; G01R 19/0053; G01R 27/02; A61B 5/053; A61B 5/0535; A61B 5/0816; A61B 5/7214

(Continued)

(56) References Cited

U.S. PATENT DOCUMENTS

| 4,283,794 A | * | 8/1981 | Underhill | G01R 27/16 |
| | | | | 324/619 |
| 8,653,828 B2 | * | 2/2014 | Hancock | A61B 18/18 |
| | | | | 324/601 |
| 2017/0007186 A1 | * | 1/2017 | Baek | A61B 5/0535 |

FOREIGN PATENT DOCUMENTS

| EP | 2200692 | 6/2010 |
| EP | 2200692 A2 | 6/2010 |

(Continued)

OTHER PUBLICATIONS

Li, Hui, et al., "A High Accuracy and High Sensitivity System Architecture for Electrical Impedance Tomography System", IEEE Asia Pacific Conference on Circuits and Systems (APCCAS), Chengdu, CN, (Oct. 2018), 4 pgs.

(Continued)

*Primary Examiner* — Tung X Nguyen
*Assistant Examiner* — Robert P Alejnikov, Jr.
(74) *Attorney, Agent, or Firm* — Schwegman Lundberg & Woessner, P.A.

(57) ABSTRACT

A device having an impedance measurement circuit that allows for reduction of flicker noise can be implemented in a variety of applications. A carrier suppression technique can be implemented that substantially removes the carrier signal with removal of noise artifacts associated with the carrier signal from sidebands of the carrier signal. Carrier suppression in an AC impedance measurement circuit can be implemented by sensing a carrier signal of the measurement circuit at a transmit location of the measurement circuit and subtracting a weighted version of the carrier signal at a receive location of the measurement circuit. One or more compensation impedances can be used such that the sidebands of the carrier signal are received with the carrier signal suppressed with respect to the receive location.

19 Claims, 6 Drawing Sheets

(58) Field of Classification Search
USPC .......................................................... 324/650
See application file for complete search history.

(56) References Cited

FOREIGN PATENT DOCUMENTS

| EP | 2653846 | 10/2013 |
|---|---|---|
| EP | 2653846 A1 | 10/2013 |
| WO | 2021245108 | 12/2021 |
| WO | WO-2021245108 A1 | 12/2021 |

OTHER PUBLICATIONS

"International Application Serial No. PCT/EP2021/064722, International Search Report dated Oct. 4, 2021", 4 pgs.
"International Application Serial No. PCT/EP2021/064722, Written Opinion dated Oct. 4, 2021", 7 pgs.

\* cited by examiner

US 11,448,673 B2

REDUCTION OF NOISE IN IMPEDANCE MEASUREMENT CIRCUITS

PRIORITY APPLICATION

This application claims the benefit of priority to U.S. Provisional application Ser. No. 63/032,913 filed 1 Jun. 2020, which is incorporated herein by reference in its entirety.

FIELD OF THE DISCLOSURE

This document relates to impedance measurement circuits and in particular to reduction of flicker noise in impedance measurement circuits.

BACKGROUND

Flicker noise is a relatively low frequency noise for which the noise power is inversely proportional to the frequency. Flicker noise is also referred to as 1/f noise. There are dynamic techniques such as chopping that can move the noise components to a high frequency. A limitation of chopping is that it may not be practicable to chop all components that are significant sources of 1/f noise. For signal applications in which the signal of interest is a low frequency signal, the noise shifted to a higher frequency effectively eliminates the 1/f noise problem. In other approaches, effects of 1/f noise can be modeled with the designs in an integrated circuit generated with margins to account for such noise. In some applications, tolerances in fabrication may not provide acceptable yields such that unacceptable noise may require that the manufacture process to increase testing. New circuit designs to account for or eliminate 1/f noise, while performing the desired application, can enhance the ability to provide the desired circuit with increased yield of manufacturing.

SUMMARY OF THE DISCLOSURE

A device having an impedance measurement circuit that allows for reduction of noise can be implemented in a variety of applications. In an alternating current (AC) impedance measurement circuit, gain instability in a channel can modulate a carrier signal into the useful sidebands of the carrier signal. A carrier suppression technique is implemented that substantially removes the carrier signal and therefore removes the noise artifacts from the sidebands. Carrier suppression in an AC impedance measurement circuit can be implemented by sensing a carrier signal of the measurement circuit at a transmit location of the measurement circuit and subtracting a weighted version of the carrier signal at a receive location of the measurement circuit.

For example, in certain embodiments, an impedance measurement device can be provided that discloses: a transmit port to drive a carrier signal to a sample under test; a receive port to receive sidebands of the carrier signal in response to modulation of the carrier signal from the sample under test; and a compensation impedance coupled between the transmit port and the receive port such that the sidebands of the carrier signal are received with the carrier signal suppressed with respect to the receive port.

In certain embodiments, a method of flicker noise reduction in an impedance measurement circuit can be provided that discloses: transmitting a carrier signal to a sample under test; and receiving sidebands of the carrier signal in response to modulation of the carrier signal from the sample under test with the carrier signal suppressed in the reception of the sidebands using compensation impedances coupled between transmission ports and receive ports of the impedance measurement circuit.

In certain embodiments, a device, having an impedance measurement circuit, can be provided that discloses: a means to transmit a carrier signal to a sample under test; a means to receive sidebands of the carrier signal in response to modulation of the carrier signal from the sample under test; and a means to suppress the carrier signal in the reception of the sidebands, with the means to suppress the carrier signal coupled between the means to transmit the carrier signal and the means to receive the sidebands of the carrier signal.

BRIEF DESCRIPTION OF THE DRAWINGS

The drawings, which are not necessarily drawn to scale, illustrate generally, by way of example, but not by way of limitation, various embodiments discussed in the present disclosure.

DETAILED DESCRIPTION

The following provides a discussion of example embodiments of an impedance measurement device having components to address noise in measurement signals, in accordance with the teachings herein.

In measurement apparatus in which the measurement is directed to sensing a parameter having a small frequency, 1/f noise can cause unacceptable errors in the measurement. Consider a respiration measurement of an individual. In a respiration measurement, electrodes are used to measure for impedance across the individual's chest to detect respiration rate. An AC carrier signal, for example having a frequency 50 kiloHertz, which is a representative frequency, can be applied to the electrodes. A representative impedance of an individual's chest is about 2 kΩ. As the individual breathes, the impedance of the chest is modulated, which provides a respiration signal of about one ohm modulation of the 2 kΩ chest impedance. Apnea is any sudden cessation of breathing for ten seconds or longer, which can be monitored in a respiration measurement. It is desired to not miss an apnea event that is catastrophic or to spuriously detect an apnea event. A cessation of breathing is indicated if there is no significant change in signal in the respiration band for 10 seconds. The respiration frequency is typically 0.3 Hz. If there is noise in the measurement circuit that exceeds say 20 mΩ, root mean squared, a decision, generated from a measurement, may spuriously be that the patient is breathing and alarms that should be raised are not raised. For such measurements, flicker noise should be substantially reduced or eliminated.

In AC measurements of an impedance in which the impedance is modulated, such as in a respiration measurement, the data of interest is in sidebands to an AC signal applied to measure the impedance. However, gain instability in a channel of the AC impedance measurement circuit can modulate a carrier signal into the useful sidebands of the carrier signal, causing 1/f noise for low frequency measurements. Since the useful information of the modulated impedance is in the sidebands, removal of the carrier signal at a sensing location is acceptable. Carrier suppression can be implemented that substantially removes the carrier signal and therefore removes the noise artifacts from the sidebands. Such carrier suppression can be implemented by sensing the carrier signal at a transmit location of the measurement circuit and subtracting a weighted version of the carrier signal at a receive location of the measurement circuit.

Figure 1:
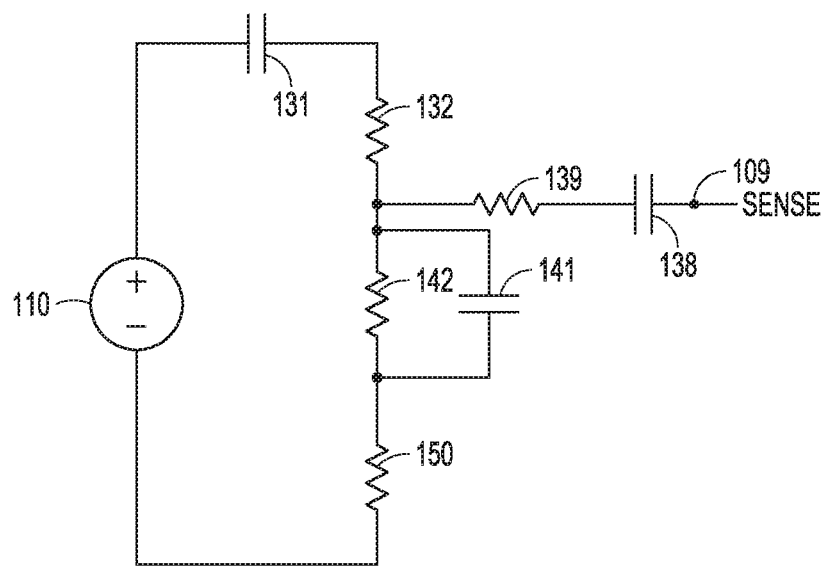
FIG. 1 illustrates a single ended, half circuit model of an application circuit to measure impedance of a test sample, associated with various embodiments.

FIG. 1 illustrates a single ended, half circuit model of an application circuit to measure impedance of a test sample 150. This model of an application circuit is appropriate for a 50 kHz respiration measurement of an individual with the test sample 150 being a real body of the individual, that is, resistance 150 being resistance of a real body. A respiration measurement is a procedure in which a respiratory rate in individuals is typically measured by counting the number of breaths per minute through determining how many times the chest rises. The motion of the chest can cause modulation of the resistance associated with the real body resistance of the individual. In a non-limiting example, this model includes an AC drive voltage source 110 that can produce a carrier signal as a sine wave at 50 kHz. Test sample 150, which can be a real body, can have a direct current (DC) resistance of 75Ω. The drive voltage source 110 can be coupled to an electrode connected to the test sample 150 via a capacitance 131 and drive resistance 132. The capacitance 131 can have a value of 1 nF and the drive resistance 132 can have a resistance value of 25 kW. The electrode can have an impedance given by an electrode resistance 142 of 900Ω in parallel with an electrode capacitor 141 having a capacitance of 1 nF. The measurement can be sensed at a sense node 109 coupled to a node, at which the drive resistance 132 couples to the electrode, by a sense resistance 139 of 50 kΩ in series with a capacitor 138 having a capacitance of 1 nF.

The electrode impedance is primarily in-phase. Not shown in this figure, respiration by the individual modulates both the body and electrode impedances, typically by about 1Ω modulation in the 1 kΩ combined impedance of the electrode and the body.

There can be excess noise associated with the measurement of the test sample 150 from the drive voltage source 110 and modulation of the test sample 150. The excess noise can be modelled as gain instability. In various embodiments, the excess noise can be modelled as an instability in channel gain. For example, in a worst case die, this instability may be of the order of 50 ppm and may have a step-like random telegraph signal (RTS) behaviour. While this noise is recorded in mΩ of variability, this mΩ variability can be modulated by changing the impedance between sense nodes (FIG. 1 is a modelled application half-circuit). With respect to this modulation, a number of approaches can be implemented for minimizing the noise. In one approach, a known impedance can be introduced between the sense nodes, and the resulting change in noise can be used to determine the noise. Alternatively, as this is a differential system, a negative impedance can be synthesized between the sense nodes to cancel some of this noise. Reference to positive and negative impedance refers to classifying the manner in which energy is processed. Positive impedance refers to consuming energy, while negative impedance refers to producing energy. With positive impedance referring to ordinary impedance, negative impedance refers to the opposite situation or opposite impedance. For instance, negative impedance can symbolize an increasing voltage opposition, while positive impedance can symbolize decreasing voltage opposition.

Figure 2:
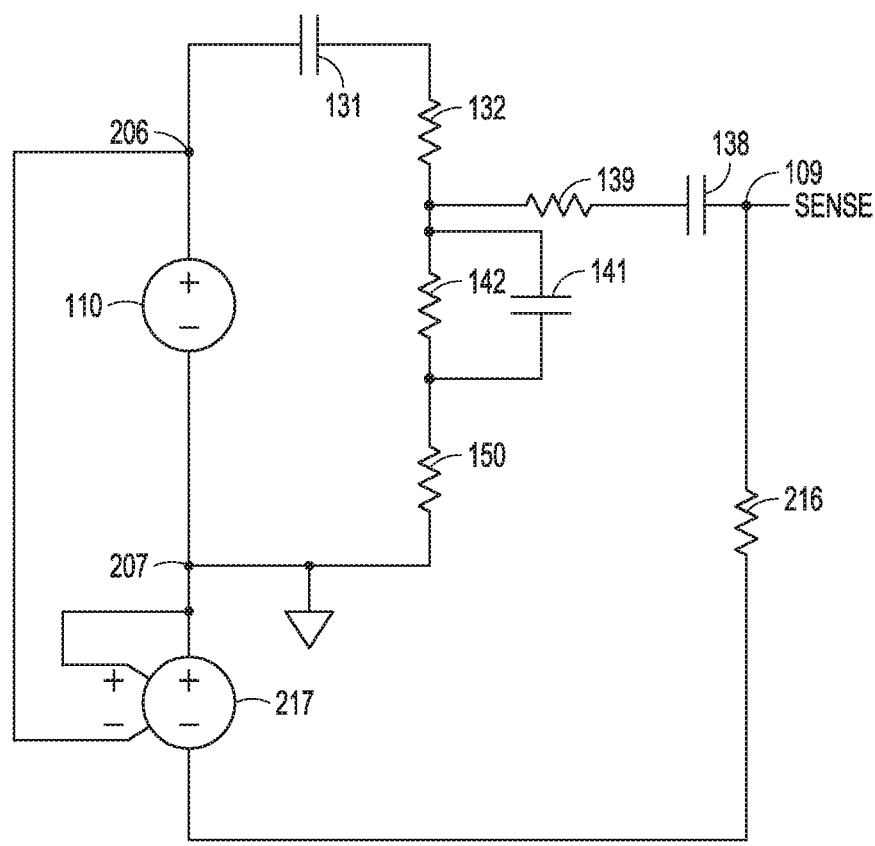
FIG. 2 show the application circuit of FIG. 1 with an added resistor and added drive voltage source, associated with various embodiments.

FIG. 2 show the application circuit of FIG. 1 with an added resistor 216 and added drive voltage source 217. In operation, the added resistor 216 can pull the sense node 109 towards the negative drive voltage source 217. The negative drive voltage source 217 is coupled to node 207, which is coupled to test sample 150, and is coupled to the added resistor 216 that acts as a cancel resistance. The added resistor 216 has a resistance value of R_Cancel. With the example components values of the example above in FIG. 1, R_Cancel can be 1.37 MΩ. Optimally, R_Cancel can be adjusted to exactly (in-phase) cancel carrier content at the sense node 109 so as to minimize noise. As a rule of thumb, cancellation can occur, approximately, with the following parameters implemented:

$$R\_Cancel/R\_Sense = R\_Drive/R\_Body$$

where R_Body is the combined impedance of the electrode (electrode resistance 142 in parallel with electrode capacitor 141) and the impedance of the real body (for example, resistance 150). R_Sense is the value of sense resistance 139, and R_Drive is the resistance value of the drive resistance 132. R_Cancel acts to cancel the carrier at the sense node 109, but not the sidebands, from modulation of test sample 150, where the sidebands have the respiration information for test sample 150 being a real body. The respiration signal can be attenuated by a small factor, approximately R_Cancel/(R_Cancel+R_Sense), which should be less than 0.5 db for the component values of the circuit elements of FIG. 2.

Added resistor 216 having R_Cancel value can be implemented as an on-chip resistive digital-to-analog converter (RDAC) without affecting pinout. For balance in a differential circuit, positive and negative RDACS with resistance value of R_Cancel can be implemented, where negative RDACS means an RDAC on the negative side of the differential circuit. The RDAC can cancel only the in-phase component of the carrier from drive source 110. If the quadrature component of the waveform at the sense node 109 is too large, then it can be minimized using a capacitive digital-to-analog converter (CAPDAC), in a similar position to the RDAC. The use of a RDAC and a CAPDAC is not mutually exclusive. In some instances, both a RDAC and a CAPDAC can be used to cancel both in-phase and quadrature components of a carrier signal.

Figure 3:
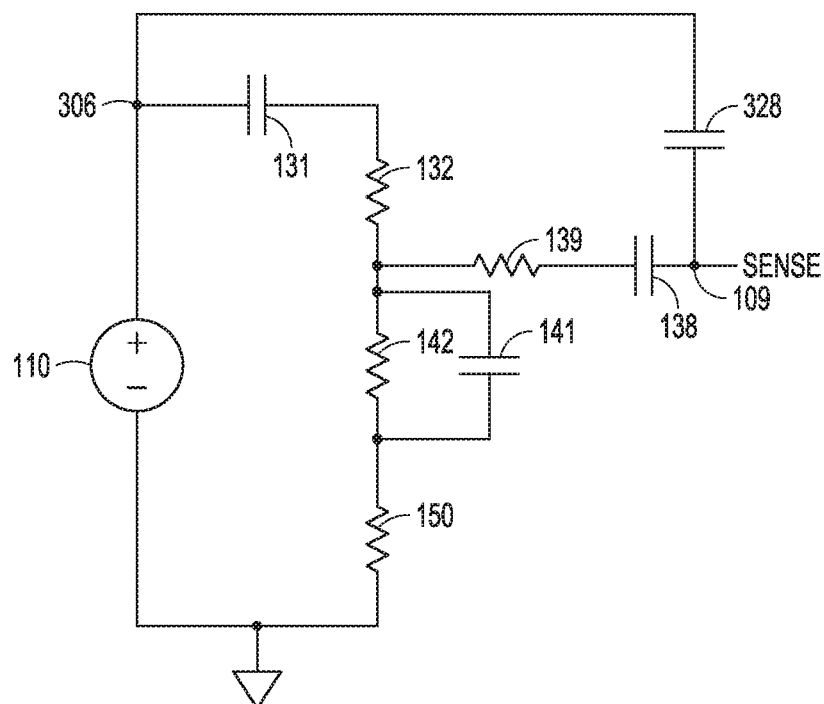
FIG. 3 shows the application circuit of FIG. 1 with a capacitor introduced to allow measurement of the instantaneous channel gain, according to various embodiments.

FIG. 3 shows the application circuit of FIG. 1 with a capacitor 328 introduced to allow measurement of the instantaneous channel gain. With the application circuit part of a respiration measurement, this allows measurement of the instantaneous channel gain separate from the respiration signal. Capacitor 328 can be implemented as a calibration capacitor (C_Cal). With the example components values of the example above in FIG. 1, capacitor 328 can have a value of 2 pF. Capacitor 328 is coupled between node 306 to which AC drive source 110 is coupled and sense node 109. According to a model with respect to noise, gain error affects both in-phase and quadrature measurements in the same proportion. Respiration of the real body, providing resistance 150, should have a stronger effect on the in-phase measurement than it does on the quadrature measurement with the body and electrodes being primarily resistive at the frequencies of the example of FIG. 1. Together, measurements of both in-phase and quadrature can allow separation of the respiration signal from the noise. With the in-phase and quadrature transfer functions for respiration and noise to the sense node being distinct, classical noise cancellation strategies can be used to separate noise from respiration signal.

Figure 4A:
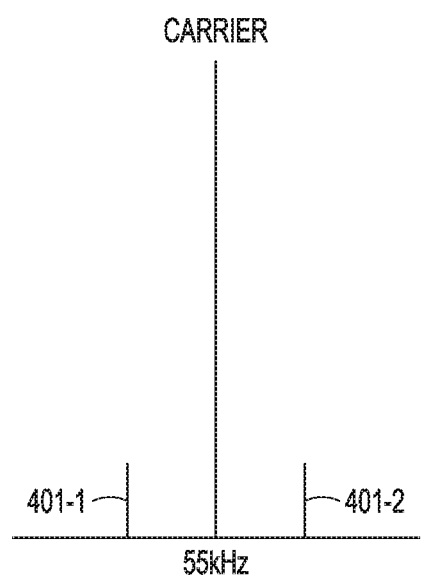
FIG. 4A shows a relationship of an applied carrier signal and expected sidebands in a respiration measurement of an individual, according to various embodiments.
Figure 4B:
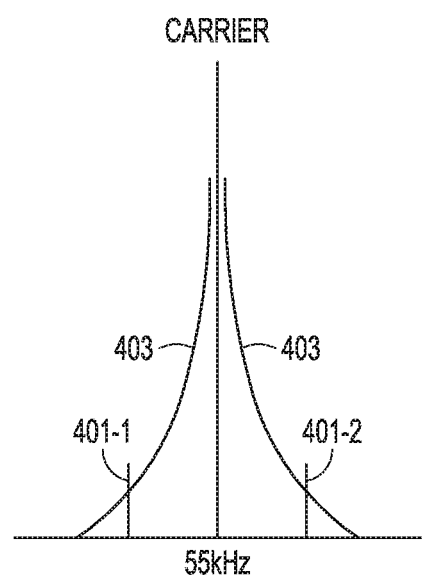
FIG. 4B shows spread the carrier frequency of FIG. 4A to the sidebands due to noise, according to various embodiments.

FIG. 4A shows a relationship of an applied carrier signal and expected sidebands in a respiration measurement of an individual. Sidebands 401-1 and 401-2 to the carrier signal are produced due to modulation of the resistance of the individual's body by the respiration activity such as breathing of the individual. In this example, a carrier signal at 55 kHz is applied with the sidebands of the respiration being at −66 dBc with a 0.3 Hz offset from the carrier signal. These sidebands 401-1 and 401-2 provide the information for the respiration measurement. However, noise, such as flicker noise, associated with the carrier signal can effectively spread the carrier frequency to the sidebands 401-1 and 401-2 as shown in FIG. 4B. With flicker noise induced gain instability, from channels that drive the carrier signal to the body of the individual, producing carrier spread 403 into the respiration bands that are the sidebands 401-1 and 401-2, errors from the respiration measurement can occur. To remove the noise associated with the carrier signal, the carrier signal and its noise can be suppressed at sensing nodes of an impedance measurement device used in the respiration measurement of an individual.

Figure 5:
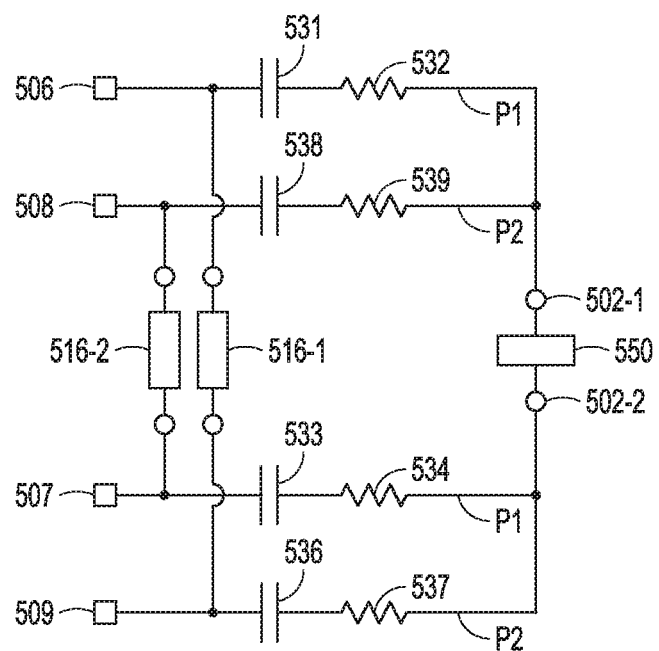
FIG. 5 illustrates an example arrangement for an impedance measurement device for measuring AC impedance of a sample under test with the arrangement including compensation impedances to suppress a carrier signal, according to various embodiments.

FIG. 5 illustrates an embodiment of an example arrangement for an impedance measurement device for measuring AC impedance of a sample 550 under test with the arrangement including compensation impedances 516-1 and 516-2 to suppress a carrier signal. In some applications, test sample 550 may be an impedance of a body of an individual, such as a thoracic impedance. Transmit ports 506 and 507 are used to drive a carrier signal to sample 550 under test along excitation path P1, where the carrier signal is an AC signal. Receive ports 508 and 509 are used to receive sidebands of the carrier signal in response to modulation of the carrier signal from the sample 550 under test with the receive ports 508 and 509 coupled to path P2 that provides a sense path. The impedance of sample 550 under test can include the electrodes that provide connection to path P1. The impedance of the electrodes can be a known value, which can be determined in calibration procedures or testing prior to measurement of sample 550 under test.

Path P1 can include capacitors 531 and 533 to block a DC component of the AC carrier signal. Path P1 can include a resistance 532 in series with capacitor 531 coupled to a node 502-1 at one end of sample 550 under test and can include a resistance 534 in series with capacitor 533 coupled to a node 502-2 at another end of sample 550 under test, opposite the end coupled to resistance 532. Nodes 502-1 and 502-2 can be part of electrodes to sample 550 under test. Path P2 can include capacitors 536 and 538 to block a DC component in this sense path. Path P2 can include a resistance 539 in series with capacitor 538 coupled to node 502-1 at one end of sample 550 under test and a resistance 537 in series with capacitor 536 coupled to node 502-2 at the other end of sample 550 under test, opposite the end coupled to resistance 539.

The AC impedance of sample 550 under test is associated with modulation of the static (DC) impedance of sample 550 under test. With the sample 550 under test being an individual undergoing a respiration measurement, breathing by the individual can cause modulation of the static impedance of the individual, such as resistance across the individual's chest. This modulation modulates the carrier signal applied to the individual, and the sensing of the effect of the modulation by the breathing can be measured from input to receive ports 508 and 509. The information is provided by sidebands of the carrier signal caused by the modulation of the impedance of the sample 550 under test.

To remove the noise associated with the carrier signal, compensation impedances 516-1 and 516-2 can be implemented to suppress the carrier signal and its noise at the receive ports 508 and 509 for sensing. Compensation impedances 516-1 and 516-2 can also be referred to as cancellation impedances. The AC measurement arrangement with compensation impedances is not limited to respiration measurements.

Compensation impedances 516-1 and 516-2 are coupled between the transmit ports 506 and 507 and the receive ports 508 and 509 such that the sidebands of the carrier signal are received with the carrier signal suppressed at the receive ports 508 and 509. Compensation impedances 516-1 and 516-2 can be coupled between the transmit ports 506 and 507 and the receive ports 508 and 509 such that the carrier signal suppression results from a subtraction operation. Impedance 516-1 can be coupled between transmit port 506 and receive port 509 with impedance 516-2 coupled between receive port 508 and transmit port 507.

Compensation impedances 516-1 and 516-2 can be selected to match to a network coupling transmit ports 506 and 507 and receive ports 508 and 509 to sample 550 under test. The network can include capacitors 531, 533, 536, and 538, resistances 532, 534, 537, and 539, and the impedances associated with sample 550 under test. The impedances associated with sample 550 under test can include impedances of connecting electrodes and impedance of sample 550 under test. In a matching procedure, the impedance of sample 550 under test can be the unmodulated resistance of sample 550. Compensation impedances 516-1 and 516-2 can be selected such that a first ratio of the compensation impedances 516-1 and 516-2 to first impedances coupled to the receive ports 508 and 509 is approximately equal to a second ratio of second impedances, coupled to the transmit ports 506 and 507, to a combination of electrode impedances to sample 550 under test and sample impedance of sample 550 under test. Compensation impedances 516-1 and 516-2 can be programmable impedances.

As the modulation of the sample 550 under test deceases, the modulation frequency decreases with the difference in frequency between the carrier frequency and the sidebands decreasing. With the modulation frequency becoming vanishingly small, the impedance of the sample 550 under test approaches the static impedance of the sample 550 under test. The use of sidebands for measurement can be replaced by the impedance measurement device using the compensation impedances 516-1 and 516-2 reporting non-modulated impedance of the sample 550 under test that can be pre-determined in a calibration procedure.

Figure 6:
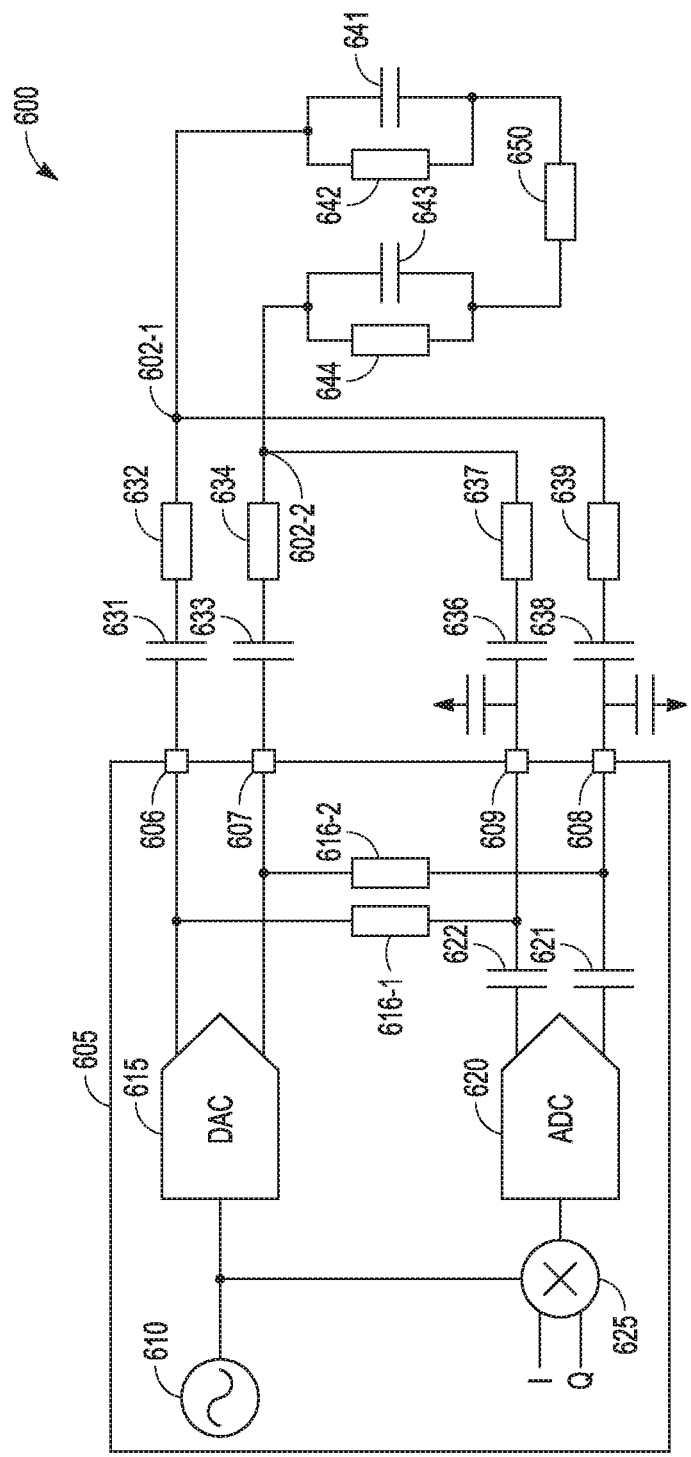
FIG. 6 is a block diagram of an impedance measurement device providing suppression of flicker noise in AC impedance measurement of a sample that is under test, according to various embodiments.

FIG. 6 is a block diagram of an impedance measurement device 600 providing suppression of flicker noise in AC impedance measurement of a sample 650 that is under test. In various embodiments, sample 650 can be a real body of an individual undergoing a test such as a respiration measurement. Impedance measurement device 600 can include a structure 605 having transmit ports 606 and 607 and receive ports 608 and 609 that can be coupled to sample 650. Structure 605 can be implemented as an integrated circuit or a portion of an integrated circuit. Transmit ports 606 and 607 are used to drive a carrier signal to sample 650, where the carrier signal is an AC signal. Receive ports 608 and 609 are used in sensing the impedance of sample 650 in which sidebands of the carrier signal are sensed in response to modulation of the carrier signal from the sample 650. Connection to sample 650 can be made via electrodes coupled to different ends of sample 650. One electrode coupled to sample 650 can include electrical properties corresponding to a resistance 642 and a capacitor 641. Another electrode coupled to a different end of sample 650 can include electrical properties corresponding to a resistance 644 and a capacitor 643.

In various embodiments, a carrier signal driven from transmit ports 606 and 607 include a DC component that is to be blocked from exciting sample 650. For example, in respiration measurements, DC excitation of a body of an individual is to be avoided. Capacitors 631 and 633 are used to block a DC component of the AC carrier signal from being directed to sample 650. The path between the electrodes to sample 650 and transmit ports 606 and 607 can include a resistance 632 in series with capacitor 631 coupled to one of the electrodes to sample 650 at node 602-1 and can include a resistance 634 in series with capacitor 633 coupled to the other of the electrodes to sample 650 at node 602-2. The path between the electrodes to sample 650 and receive ports 608 and 609 for sensing can include capacitors 636 and 638 to block a DC component in this sense path. The path between the electrodes to sample 650 and receive ports 608 and 609 can include a resistance 639 in series with capacitor 638 coupled to node 602-1 and can include a resistance 637 in series with capacitor 636 coupled to node 602-2. At the receive nodes 608 and 609, capacitors to ground can be used.

Structure 605 can include an AC drive signal source 610 that can produce a carrier signal to excite sample 650. The carrier signal is input to a digital-to-analog converter (DAC) 615, which has two outputs with one output coupled to transmit port 606 and the other output coupled to transmit port 607. DAC 615 can include one or more amplifier components or can be implemented as an amplifier. Structure 605 can also include an analog-to-digital converter (ADC) 620 coupled to receive ports 608 and 609 for sensing the AC impedance measurement of sample 650. Receive port 609 can be coupled optionally to an input of ADC 620 by a capacitor 622 and receive port 608 can be coupled optionally to another input of ADC 620 by a capacitor 621.

Excess noise in the signal exciting sample 650 can be caused by instability in channel gain of the output channels of DAC 615. This excess noise can be exhibited as flicker noise in the AC impedance measurement of sample 650. This noise can cause the carrier signal to spread, making recovery of sidebands to the carrier signal modulated by the sample 650 subject to errors. Such spreading is similar to that of FIG. 4B. To recover the desired sidebands that provide information regarding the AC impedance of sample 650, the carrier signal and its associated noise can be suppressed for operation by ADC 620.

To remove the noise associated with the carrier signal, compensation impedances 616-1 and 616-2 can be implemented to suppress the carrier signal and its noise at the receive ports 608 and 609 for sensing. Compensation impedances 616-1 and 616-2 can also be referred to as cancellation impedances. Compensation impedances 616-1 and 616-2 are coupled to receive ports 609 and 608, respectively.

Compensation impedances 616-1 and 616-2 can be coupled between the transmit ports 606 and 607 and the receive ports 608 and 609 such that the sidebands of the carrier signal are received with the carrier signal suppressed with respect to the receive ports 608 and 609. Compensation impedances 616-1 and 616-2 can be coupled between the transmit ports 606 and 607 and the receive ports 608 and 609 such that the carrier signal suppression results from a subtraction operation. Impedance 616-1 can be coupled between transmit port 606 and receive port 609 with impedance 616-2 coupled between receive port 608 and transmit port 607. Compensation impedances 616-1 and 616-2 can be selected to match to a network coupling transmit ports 606 and 607 and receive ports 608 and 609 to sample 650. The network can include capacitors 631, 633, 636, and 638, resistances 632, 634, 637, and 639, and the impedances associated with sample 650. The impedances associated with sample 650 can include impedances of connecting electrodes and impedance of sample 650. In a matching procedure, the impedance of sample 650 can be the unmodulated resistance of sample 650. Compensation impedances 616-1 and 616-2 can be selected such that a first ratio of the compensation impedances 616-1 and 616-2 to first impedances coupled to the receive ports 608 and 609 is approximately equal to a second ratio of second impedances, coupled to the transmit ports 606 and 607, to a combination of electrode impedances to sample 650 and sample impedance of sample 650. Compensation impedances 616-1 and 616-2 can be programmable impedances.

The two outputs of DAC 615 coupled to the transmit ports 606 and 607 can provide the carrier signal as a differential signal with one of the two outputs coupled to transmit port 606 arranged as a positive drive node and the other one of the two outputs coupled to transmit port 607 arranged as a negative drive node. The two inputs of ADC 620 can be coupled to the receive ports 609 and 608 with one of the two inputs coupled to receive port 608 arranged as a positive sense node and the other one of the two inputs coupled to receive port 609 arranged as a negative sense node. Compensation impedance 616-1 is coupled between the positive drive node 606 and the negative sense node 609. Compensation impedance 616-2 is coupled between the negative drive node 607 and the positive sense node 608. This arrangement of positive and negative nodes can provide for the compensation impedances 616-1 and 616-2 to effectively suppress the carrier signal from a subtraction operation. In other embodiments, ADC 620 can be structured in a single-ended arrangement and compensation impedance 616-1 can be omitted.

Structure 605 can include a mixer 625. Mixer 625 mixes the carrier signal from AC drive signal source 610 and an output of ADC 620. Mixer 625 can provide two outputs: an in-phase signal, I, and a quadrature phase signal, Q. Structure 605 can include other components that operate signals I and Q to analyze the sensed signals to make one or more impedance measurements of sample 650. Alternatively, I and Q can be provided to a structure separate from structure 605, for example, to a die that is different from a die on which structure 605 is located.

Figure 7:
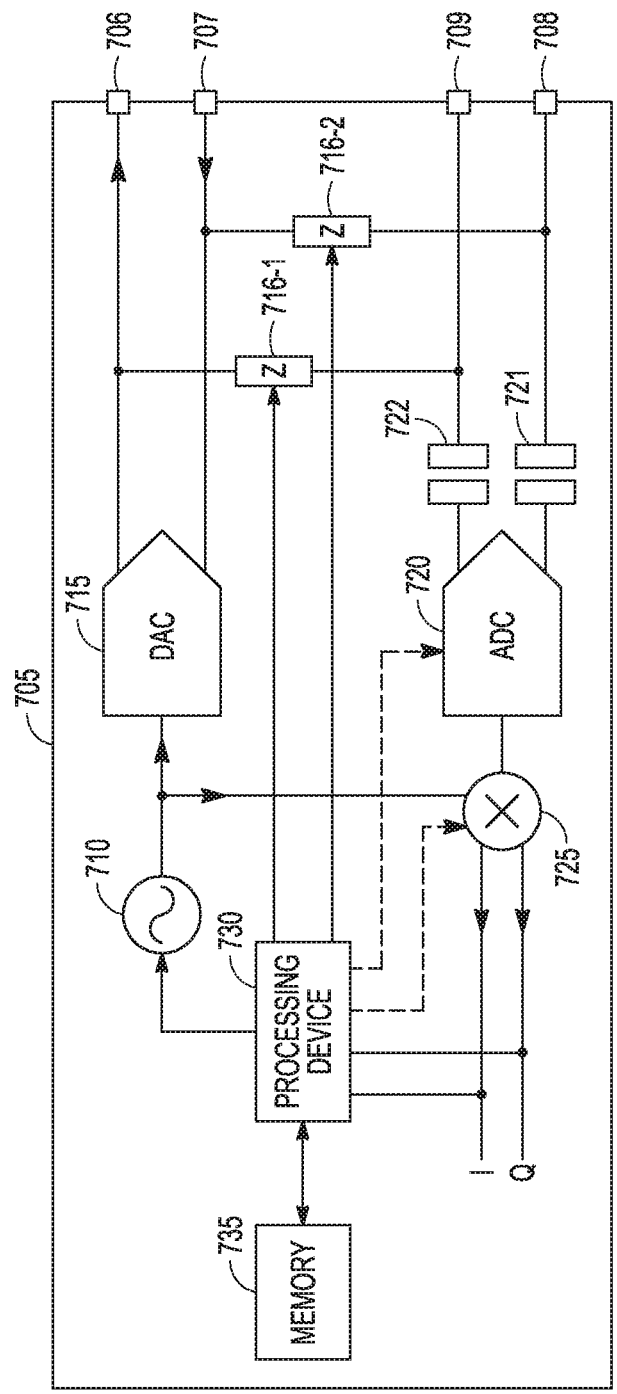
FIG. 7 is a block diagram of a structure having components to provide suppression of flicker noise in AC impedance measurement of a sample coupled to the structure, according to various embodiments.

FIG. 7 is a block diagram of a structure 705 having components to provide suppression of flicker noise in AC impedance measurement of a sample coupled to structure 705. The suppression of the flicker noise can be implemented by suppression of a carrier signal received from the sample probed by the carrier signal driven from the structure 705 to the sample. Structure 705 can include components similar to components of structure 605 of FIG. 6 in design or operation. Structure 705 can include transmit ports 706 and 707 and receive ports 708 and 709 that can be coupled to a sample under test. In various embodiments, a sample under test, which can be measured using structure 705, can be a real body of an individual undergoing a test such as a respiration measurement. Structure 705 can be implemented as an integrated circuit or a portion of an integrated circuit. Transmit ports 706 and 707 are used to drive a carrier signal to a sample under test, where the carrier signal is an AC signal. Receive ports 708 and 709 are used in sensing the impedance of the sample under test in which sidebands of the carrier signal are sensed in response to modulation of the carrier signal by the sample.

Structure 705 can include an AC drive signal source 710 that can produce a carrier signal to excite a sample under test. The carrier signal is input to a DAC 715, which has two outputs with one output coupled to transmit port 706 and the other output coupled to transmit port 707. DAC 715 can include one or more amplifier components or can be implemented as an amplifier. Structure 705 can also include an ADC 720 coupled to receive ports 708 and 709 for sensing the AC impedance measurement of the sample under test. Receive port 709 can be coupled optionally to an input of ADC 720 by a capacitor 722 and receive port 708 can be coupled optionally to another input of ADC 720 by a capacitor 721.

Excess noise in the signal exciting a sample under test can be caused by instability in channel gain of the output channels of DAC 715. This excess noise can be exhibited as flicker noise in the AC impedance measurement of the sample. This noise can cause the carrier signal to spread, making recovery of sidebands to the carrier signal modulated by the sample subject to errors. Such spreading is similar to that of FIG. 4B. To recover the desired sidebands that provide information regarding the AC impedance of the sample under test, the carrier signal and its associated noise can be suppressed from operation by ADC 720.

To remove the noise associated with the carrier signal, compensation impedances 716-1 and 716-2 can be implemented to suppress the carrier signal and its noise at the receive ports 708 and 709 for sensing. Compensation impedances 716-1 and 716-2 can also be referred to as cancellation impedances. Compensation impedances 716-1 and 716-2 are coupled to receive ports 709 and 708, respectively.

Compensation impedances 716-1 and 716-2 can be coupled between the transmit ports 706 and 707 and the receive ports 708 and 709 such that the sidebands of the carrier signal are received with the carrier signal suppressed with respect to the receive ports 708 and 709. Compensation impedances 716-1 and 716-2 can be coupled between the transmit ports 706 and 707 and the receive ports 708 and 709 such that the carrier signal suppression results from a subtraction operation. Impedance 716-1 can be coupled between transmit port 706 and receive port 709 with impedance 716-2 coupled between receive port 708 and transmit port 707.

Compensation impedances 716-1 and 716-2 can be selected to match to a network coupling transmit ports 706 and 707 and receive ports 708 and 709 to a sample under test. The network, to which structure 705 can be coupled, can include impedances, impedance associated with the sample, and impedances of connecting electrodes to the sample. In a matching procedure, the impedance of the sample under test can be the unmodulated resistance of the sample. Compensation impedances 716-1 and 716-2 can be selected with respect to a first ratio of the compensation impedances 716-1 and 716-2 to a first set of impedances of the network coupled to the receive ports 708 and 709 being substantially equal to a second ratio of a second set of impedances coupled to the transmit ports 706 and 707 to a combination of electrode impedances to the sample under test and sample impedance of the sample under test. Compensation impedances 716-1 and 716-2 can be programmable impedances.

The two outputs of DAC 715 coupled to the transmit ports 706 and 707 can provide the carrier signal as a differential signal with one of the two outputs coupled to transmit port 706 arranged as a positive drive node and the other one of the two outputs coupled to transmit port 707 arranged as a negative drive node. The two inputs of ADC 720 coupled to the receive ports 709 and 708 can be provided with one of the two inputs coupled to receive port 708 arranged as a positive sense node and the other one of the two inputs coupled to receive port 709 arranged as a negative sense node. Compensation impedance 716-1 is coupled between the positive drive node 706 and the negative sense node 709. Compensation impedance 716-2 is coupled between the negative drive node 707 and the positive sense node 708. This arrangement of positive and negative nodes can provide for the compensation impedances 716-1 and 716-2 to effectively suppress the carrier signal from a subtraction operation. In other embodiments, ADC 720 can be structured in a single ended arrangement and compensation impedance 716-1 can be omitted.

Structure 705 can include a mixer 725. Mixer 725 mixes the carrier signal from AC drive signal source 710 and an output of ADC 720. Mixer 725 can provide two outputs: an in-phase signal, I, and a quadrature phase signal, Q, which outputs are produced from mixing the carrier signal and the output of ADC 720 that is coupled to receive ports 708 and 709. Structure 705 can include other components that operate on signals I and Q to analyze the sensed signals to make one or more impedance measurements of the sample under test. Alternatively, I and Q can be provided to a structure separate from structure 705, for example, to a die that is different from a die on which structure 705 is located.

Structure 705 can include a processing device 730 and a memory 735 coupled to the processing device 730. Memory 735 is a machine-readable storage device, which stores instructions that when executed by processing device 730 causes performance of operations. Processing device 730 can be implemented as one or more processors, such as but not limited to one or more digital signal processors (DSPs). Processing device 730 can execute a number of operations associated with AC impedance measurement of a sample coupled to structure 705. Operations executed by processing device 730 can include operation on the I and Q signals from mixer 725. Operations executed by processing device 730 can include controlling compensation impedances 716-1 and 716-2 structured as programmable impedances. Processing device 730 can execute operations to iteratively adjust compensation impedances 716-1 or 716-2 to substantially minimize the carrier signal observed at receive ports 708 and 709. Processing device 730 can execute operations to adjust the compensation impedances 716-1 and 716-2 such that a first ratio of the compensation impedances 716-1 or 716-2 to first impedances coupled to the receive ports 708 and 709 is approximately equal to a second ratio of second impedances coupled to the transmit ports 706 and 707 to a combination of electrode impedances to the sample under test and the sample impedance.

Processing device 730 can execute operations to adjust the compensation impedances 716-1 or 716-2 by adjusting a programmable resistance and a programmable capacitance of the respective compensation impedances 716-1 and 716-2. The programmable resistance of compensation impedances 716-1 and 716-2 can be implemented in a number of conventional arrangements that can be implemented in an integrated circuit. The programmable capacitance of compensation impedances 716-1 and 716-2 can be implemented in a number of conventional arrangements that can be implemented in an integrated circuit. Processing device 730 can execute operations to generate a value of impedance of the sample under test in a non-modulated state from impedance information about compensation impedances 716-1 and 716-2.

Processing device 730 can execute operations to add an estimate of one or more of compensation impedance 716-1, compensation impedance 716-2, and a combination of compensation impedances 716-1 and 716-2 to the I and Q signals output from mixer 725 by processing device 730. Processing device 730 can be arranged to control mixer 725 and ADC 720. In another approach, the estimate can be added by processing device 730 to an input of mixer 725 along with the signal from the output of ADC 720. The effect of adding the estimate to the I and Q signals is to re-constitute the output that would occur without carrier cancellation and also without the noise. This can obviate any need for additional output paths from the device to convey the estimate, and so simplifies the adoption of carrier cancellation. If the compensation impedance, which is cancelling impedance, is a capacitor, its value can be added to the Q signal after mixer 725. If the compensation impedance is a resistor, its value can be added to the I signal after mixer 725.

In various embodiments, an impedance measurement device can comprise: a transmit port to drive a carrier signal to a sample under test; a receive port to receive sidebands of the carrier signal in response to modulation of the carrier signal from the sample under test; and a compensation impedance coupled between the transmit port and the receive port such that the sidebands of the carrier signal are received with the carrier signal suppressed with respect to the receive port. The impedance measurement device can include a second transmit port, a second receive port, and a second compensation impedance arranged with the compensation impedance, the transmit port, and the receive port such that the carrier signal suppression results from a subtraction operation.

Variations of such an impedance measurement device or similar impedance measurement devices can include a number of different embodiments that may be combined depending on the application of such impedance measurement devices or the architecture of systems in which such impedance measurement devices are implemented. Such impedance measurement devices can include: the transmit port being one of two transmit ports, the receive port being one of two receive ports, the compensation impedance being one of two compensation impedances, a digital-to-analog converter, and an analog-to-digital converter. The digital-to-analog converter can have two outputs coupled to the two transmit ports to provide the carrier signal as a differential signal, with one of the two outputs coupled to one of the two transmit ports arranged as a positive drive node and the other one of the two outputs coupled to the one of the two transmit ports arranged as a negative drive node. The analog-to-digital converter can have two inputs coupled to the two receive ports, with one of the two inputs coupled to one of the two receive ports arranged as a positive sense node and the other one of the two inputs coupled to another one of the two receive ports arranged as a negative sense node. A first compensation impedance of the two compensation impedances can be coupled between the positive drive node and the negative sense node, and a second compensation impedance of the two compensation impedances can be coupled between the negative drive node and the positive sense node.

Variations of such an impedance measurement device or similar impedance measurement devices can include the compensation impedance being matched to a network coupling the transmit port and receive port to the sample under test, the network including the sample under test. The compensation impedance can be selected such that a first ratio of the compensation impedance to a first impedance coupled to the receive port is approximately equal to a second ratio of a second impedance coupled to the transmit port to a combination of electrode impedance to the sample under test and sample impedance. Variations can include the compensation impedance being a programmable impedance under control of a processing device with the processing device operable to iteratively adjust the compensation impedance to minimize the carrier signal with respect to the receive port. This iterative adjusting of the compensation impedance can be used to generate a value of impedance of the sample under test in a non-modulated state from impedance information about the compensation impedance.

Variations of such an impedance measurement device or similar impedance measurement devices can include an analog-to-digital converter coupled to the receive port; a mixer to mix the carrier signal and an output of the analog-to-digital converter to produce an in-phase signal and a quadrature phase signal: and a processing device operable to selectively add an estimate of the compensation impedance to the in-phase signal or the quadrature phase signal output from the mixer.

A processing device, integrated in the impedance measurement device or networked with the impedance measurement device, can operate on the in-phase signal and a quadrature phase signal to generate information regarding the sample under test.

A device having an impedance measurement circuit can comprise: a means to transmit a carrier signal to a sample under test; a means to receive sidebands of the carrier signal in response to modulation of the carrier signal from the sample under test; and a means to suppress the carrier signal in the reception of the sidebands, with the means to suppress the carrier signal coupled between the means to transmit the carrier signal and the means to receive the sidebands of the carrier signal. The means to transmit the carrier signal can include a positive drive node to transmit a positive drive signal to a first electrode coupled to the sample under test and a negative drive node to transmit a negative drive signal to a second electrode coupled to the sample under test opposite the coupling of the first electrode to the sample under test. The means to suppress the carrier signal can include: a first compensation impedance coupled between the positive drive node and a negative sense node of the means to receive sidebands of the carrier signal; and a second compensation impedance coupled between the negative drive node and a positive sense node of the means to receive sidebands of the carrier signal.

Variations of such a device having an impedance measurement circuit or similar device having an impedance measurement circuit can include a number of different embodiments that may be combined depending on the application of such devices having an impedance measurement circuit or the architecture of systems in which such devices having an impedance measurement circuit are implemented. Such device having an impedance measurement circuit can include the means to suppress the carrier signal to include a means to adjust the means to suppress the carrier signal. Such device having an impedance measurement circuit can include: a means to mix the carrier signal with a version of the received sidebands of the carrier signal and a means to process information. The means to process information can include means to: generate a value of impedance of the sample under test in a non-modulated state from impedance information about the means to suppress the carrier signal; and combine the value of the impedance of the sample under test in the non-modulated state with a measured impedance of the sample under test from the received sidebands.

Figure 8:
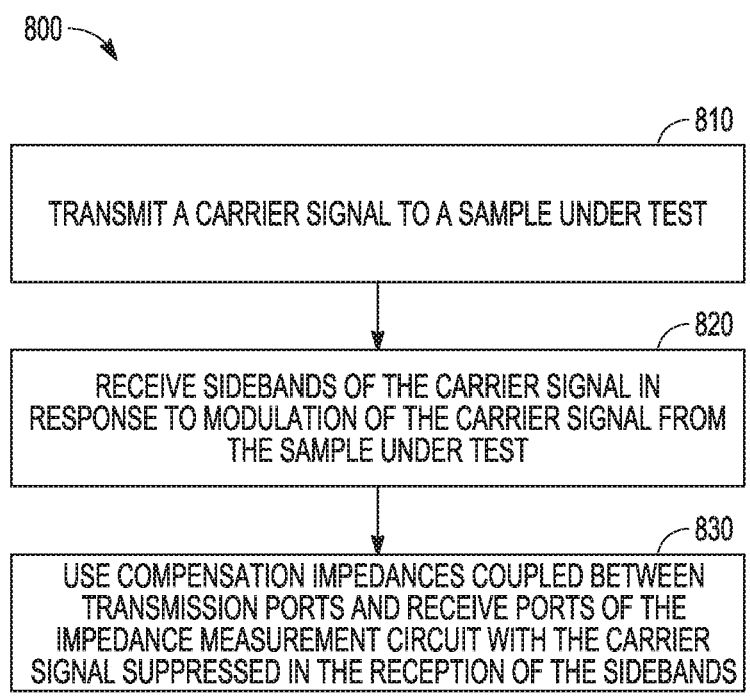
FIG. 8 is a flow diagram of features of an example method of flicker noise reduction in an impedance measurement circuit, according to various embodiments.

FIG. 8 is a flow diagram of features of an embodiment of an example method 800 of flicker noise reduction in an impedance measurement circuit. At 810, a carrier signal is transmitted to a sample under test. At 820, sidebands of the carrier signal are received in response to modulation of the carrier signal from the sample under test. At 830, compensation impedances coupled between transmission ports and receive ports of the impedance measurement circuit are used with the carrier signal suppressed in the reception of the sidebands. The suppression of the carrier signal can be implemented by using a subtraction operation.

Variations of method 800 or methods similar to the method 800 can include a number of different embodiments that may be combined depending on the application of such methods and/or the architecture of systems in which such methods are implemented. Such methods can include transmitting the carrier signal to include transmitting a positive drive signal to a first electrode coupled to the sample under test and a negative drive signal to a second electrode coupled to the sample under test opposite the coupling of the first electrode to the sample under test. A first compensation impedance of the compensation impedances can be coupled between a positive drive node of the transmission ports and a negative sense node of the receive ports. In this structure, a second compensation impedance of the compensation impedances can be coupled between the negative drive node of the transmission ports and the positive sense node of the receive ports.

Variations of the method 800 or methods similar to the method 800 can include adjusting the compensation impedances such that a first ratio of the compensation impedances to first impedances coupled to the receive ports is approximately equal to a second ratio of second impedances coupled to the transmit ports to a combination of electrode impedances to the sample under test and sample impedance. Variations of the method 800 or methods similar to the method 800 can include adjusting the compensation impedances by adjusting a programmable resistance and a programmable capacitance under control of a processing device. Further, adjusting the compensation impedances can include iteratively adjusting the compensation impedances to minimize the carrier signal at the receive ports of the impedance measurement circuit. The programmable resistance and the programmable capacitance can be implemented in a number of ways. For instance, the programmable resistance can be implemented as a number of resistances in series with each series in parallel with a switch, under control of the processing device, to selectively bypass the respective resistance. The programmable capacitance can be implemented as a set of capacitors having a common node with each capacitor in series with a switch coupled to a node common to all the switches associated with the capacitors of the set, where each switch is under control of the processing device. Other forms of programmable resistances and programmable capacitors can be used.

Variations of the method 800 or methods similar to the method 800 can include mixing the carrier signal with a version of the received sidebands of the carrier signal with the carrier signal suppressed; outputting an in-phase signal and a quadrature phase signal; and processing the in-phase signal.

The following are example embodiments of devices having an impedance measurement circuit and associated methods, in accordance with the teachings herein.

An example impedance measurement device 1 can comprise: a transmit port to drive a carrier signal to a sample under test; a receive port to receive sidebands of the carrier signal in response to modulation of the carrier signal from the sample under test; and a compensation impedance coupled between the transmit port and the receive port such that the sidebands of the carrier signal are received with the carrier signal suppressed with respect to the receive port.

An example impedance measurement device 2 can include features of example impedance measurement device 1 and can include the impedance measurement device to include a second transmit port, a second receive port, and a second compensation impedance arranged with the compensation impedance, the transmit port, and the receive port such that the carrier signal suppression results from a subtraction operation.

An example impedance measurement device 3 can include features of any of the preceding example impedance measurement devices and can include: the impedance measurement device to include: the transmit port being one of two transmit ports, the receive port being one of two receive ports, and the compensation impedance being one of two compensation impedances; a digital-to-analog converter having two outputs coupled to the two transmit ports to provide the carrier signal as a differential signal with one of the two outputs coupled to one of the two transmit ports arranged as a positive drive node and the other one of the two outputs coupled to the one of the two transmit ports arranged as a negative drive node; an analog-to-digital converter having two inputs coupled to the two receive ports with one of the two inputs coupled to one of the two receive ports arranged as a positive sense node and the other one of the two inputs coupled to another one of the two receive ports arranged as a negative sense node; a first compensation impedance of the two compensation impedances coupled between the positive drive node and the negative sense node; and a second compensation impedance of the two compensation impedances coupled between the negative drive node and the positive sense node.

An example impedance measurement device 4 can include features of any of the preceding example impedance measurement devices and can include the compensation impedance matched to a network coupling the transmit port and receive port to the sample under test, the network including the sample under test.

An example impedance measurement device 5 can include features of any of the preceding example impedance measurement devices and can include the compensation impedance selected such that a first ratio of the compensation impedance to a first impedance coupled to the receive port is approximately equal to a second ratio of a second impedance coupled to the transmit port to a combination of electrode impedance to the sample under test and sample impedance.

An example impedance measurement device 6 can include features of any of the preceding example impedance measurement devices and can include the compensation impedance being a programmable impedance under control of a processing device with the processing device operable to iteratively adjust the compensation impedance to minimize the carrier signal with respect to the receive port.

An example impedance measurement device 7 can include features of any of the preceding example impedance measurement devices and can include an analog-to-digital converter coupled to the receive port; a mixer to mix the carrier signal and an output of the analog-to-digital converter to produce an in-phase signal and a quadrature phase signal; and a processing device operable to selectively add an estimate of the compensation impedance to the in-phase signal or the quadrature phase signal output from the mixer.

An example device 8, having an impedance measurement circuit, can comprise: a means to transmit a carrier signal to a sample under test; a means to receive sidebands of the carrier signal in response to modulation of the carrier signal from the sample under test; and a means to suppress the carrier signal in the reception of the sidebands, with the means to suppress the carrier signal coupled between the means to transmit the carrier signal and the means to receive the sidebands of the carrier signal.

An example device 9, having an impedance measurement circuit, can include features of example device 8, having an impedance measurement circuit, and can include the means to transmit the carrier signal to include a positive drive node to transmit a positive drive signal to a first electrode coupled to the sample under test and a negative drive node to transmit a negative drive signal to a second electrode coupled to the sample under test opposite the coupling of the first electrode to the sample under test.

An example device 10, having an impedance measurement circuit, can include features of example devices 8 and 9, each having an impedance measurement circuit, and can include the means to suppress the carrier signal to include: a first compensation impedance coupled between the positive drive node and a negative sense node of the means to receive sidebands of the carrier signal; and a second compensation impedance coupled between the negative drive node and a positive sense node of the means to receive sidebands of the carrier signal.

An example device 11, having an impedance measurement circuit, can include features of any of the preceding example devices, having an impedance measurement circuit, and can include the means to suppress the carrier signal to include a means to adjust the means to suppress the carrier signal.

An example device 12, having an impedance measurement circuit, can include features of any of the preceding example devices, having an impedance measurement circuit, and can include a means to mix the carrier signal with a version of the received sidebands of the carrier signal; a means to process an in-phase signal generated from the means to mix the carrier signal with the version of the received sidebands of the carrier signal; and a means to process information to: generate a value of impedance of the sample under test in a non-modulated state from impedance information about the means to suppress the carrier signal; and combine the value of the impedance of the sample under test in the non-modulated state with a measured impedance of the sample under test from the received sidebands.

An example method 1 of flicker noise reduction in an impedance measurement circuit can comprise: transmitting a carrier signal to a sample under test; and receiving sidebands of the carrier signal in response to modulation of the carrier signal from the sample under test with the carrier signal suppressed in the reception of the sidebands using compensation impedances coupled between transmission ports and receive ports of the impedance measurement circuit.

An example method 2 of flicker noise reduction in an impedance measurement circuit can include features of example method 1 of flicker noise reduction in an impedance measurement circuit and can include suppression of the carrier signal by using a subtraction operation.

An example method 3 of flicker noise reduction in an impedance measurement circuit can include features of any of the preceding example methods of flicker noise reduction in an impedance measurement circuit and can include transmitting the carrier signal to include transmitting a positive drive signal to a first electrode coupled to the sample under test and a negative drive signal to a second electrode coupled to the sample under test opposite the coupling of the first electrode to the sample under test.

An example method 4 of flicker noise reduction in an impedance measurement circuit can include features of method 3 of flicker noise reduction in an impedance measurement circuit or features of any of the preceding example methods of flicker noise reduction in an impedance measurement circuit and can include a first compensation impedance of the compensation impedances being coupled between a positive drive node of the transmission ports and a negative sense node of the receive ports; and a second compensation impedance of the compensation impedances being coupled between the negative drive node of the transmission ports and the positive sense node of the receive ports.

An example method 5 of flicker noise reduction in an impedance measurement circuit can include features of any of the preceding example methods of flicker noise reduction in an impedance measurement circuit and can include adjusting the compensation impedances such that a first ratio of the compensation impedances to first impedances coupled to the receive ports is approximately equal to a second ratio of second impedances coupled to the transmit ports to a combination of electrode impedances to the sample under test and sample impedance.

An example method 6 of flicker noise reduction in an impedance measurement circuit can include features of any of the preceding example methods of flicker noise reduction in an impedance measurement circuit and can include adjusting the compensation impedances by adjusting a programmable resistance and a programmable capacitance under control of a processing device.

An example method 7 of flicker noise reduction in an impedance measurement circuit can include features of example method 6 of flicker noise reduction in an impedance measurement circuit or features of any of the preceding example methods of flicker noise reduction in an impedance measurement circuit and can include adjusting the compensation impedances to include iteratively adjusting the compensation impedances to minimize the carrier signal at the receive ports of the impedance measurement circuit.

An example method 8 of flicker noise reduction in an impedance measurement circuit can include features of example method 5 of flicker noise reduction in an impedance measurement circuit or features of any of the preceding example methods of flicker noise reduction in an impedance measurement circuit and can include mixing the carrier signal with a version of the received sidebands of the carrier signal with the carrier signal suppressed; outputting an in-phase signal and a quadrature phase signal; and processing the in-phase signal.

An example method 9 of flicker noise reduction in an impedance measurement circuit can include features of any of the preceding example methods 1-8 of flicker noise reduction in an impedance measurement circuit and can include performing functions associated with any features of example impedance measurement devices 1-7 and example devices 8-14, having an impedance measurement circuit, and any features of example impedance measurement devices and example devices having an impedance measurement circuit associated with the figures herein.

The above detailed description refers to the accompanying drawings that show, by way of illustration and not limitation, various embodiments that can be practiced. These embodiments are described in sufficient detail to enable those skilled in the art to practice these and other embodiments. Other embodiments may be utilized, and structural, logical, mechanical, and electrical changes may be made to these embodiments. The various embodiments are not necessarily mutually exclusive, as some embodiments can be combined with one or more other embodiments to form new embodiments. The above detailed description is, therefore, not to be taken in a limiting sense.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description.

What is claimed is:

1. An impedance measurement device comprising:
   a transmit port to drive a carrier signal to a sample under test;
   a receive port to receive sidebands of the carrier signal in response to modulation of the carrier signal from the sample under test; and
   a compensation impedance coupled between the transmit port and the receive port such that the sidebands of the carrier signal are received with the carrier signal suppressed with respect to the receive port;
   a mixer to mix the carrier signal with a version of the received sidebands of the carrier signal; and
   a processing device configured to:
   generate a value of impedance of the sample under test in a non-modulated state from impedance information about the means to suppress the carrier signal; and
   combine the value of the impedance of the sample under test in the non-modulated state with a measured impedance of the sample under test from the received sidebands.

2. The impedance measurement device of claim 1, wherein the impedance measurement device includes a second transmit port, a second receive port, and a second compensation impedance arranged with the compensation impedance, the transmit port, and the receive port such that the carrier signal suppression results from a subtraction operation.

3. The impedance measurement device of claim 1, wherein the impedance measurement device includes:
   the transmit port being one of two transmit ports, the receive port being one of two receive ports, and the compensation impedance being one of two compensation impedances;
   a digital-to-analog converter having two outputs coupled to the two transmit ports to provide the carrier signal as a differential signal, with one of the two outputs coupled to one of the two transmit ports arranged as a positive drive node and the other one of the two outputs coupled to the one of the two transmit ports arranged as a negative drive node;
   an analog-to-digital converter having two inputs coupled to the two receive ports, with one of the two inputs coupled to one of the two receive ports arranged as a positive sense node and the other one of the two inputs coupled to another one of the two receive ports arranged as a negative sense node;
   a first compensation impedance of the two compensation impedances coupled between the positive drive node and the negative sense node; and
   a second compensation impedance of the two compensation impedances coupled between the negative drive node and the positive sense node.

4. The impedance measurement device of claim 1, wherein the compensation impedance is matched to a network coupling the transmit port and receive port to the sample under test, the network including the sample under test.

5. The impedance measurement device of claim 1, wherein the compensation impedance is selected such that a first ratio of the compensation impedance to a first impedance coupled to the receive port is approximately equal to a second ratio of a second impedance coupled to the transmit port to a combination of electrode impedance to the sample under test and sample impedance.

6. The impedance measurement device of claim 1, wherein the compensation impedance is a programmable impedance under control of a processing device with the processing device operable to iteratively adjust the compensation impedance to minimize the carrier signal with respect to the receive port.

7. The impedance measurement device of claim 1, wherein the impedance measurement device includes:
   an analog-to-digital converter coupled to the receive port;
   wherein the mixer is configured to mix the carrier signal and an output of the analog-to-digital converter to produce an in-phase signal and a quadrature phase signal; and
   wherein the processing device is operable to selectively add an estimate of the compensation impedance to the in-phase signal or the quadrature phase signal output from the mixer.

8. A method of flicker noise reduction in an impedance measurement circuit, the method comprising:
   transmitting a carrier signal to a sample under test; and
   receiving sidebands of the carrier signal in response to modulation of the carrier signal from the sample under test;

suppressing the carrier signal in the reception of the sidebands using compensation impedances coupled between transmission ports and receive ports of the impedance measurement circuit;

mixing the carrier signal with a version of the received sidebands of the carrier signal;

generating a value of impedance of the sample under test in a non-modulated state from impedance information about the compensation impedances that suppress the carrier signal; and combining the value of the impedance of the sample under test in the non-modulated state with a measured impedance of the sample under test from the received sidebands.

9. The method of claim 8, wherein the method includes suppression of the carrier signal by using a subtraction operation.

10. The method of claim 8, wherein transmitting the carrier signal includes transmitting a positive drive signal to a first electrode coupled to the sample under test and a negative drive signal to a second electrode coupled to the sample under test opposite the coupling of the first electrode to the sample under test.

11. The method of claim 10, wherein a first compensation impedance of the compensation impedances is coupled between a positive drive node of the transmission ports and a negative sense node of the receive ports; and a second compensation impedance of the compensation impedances is coupled between the negative drive node of the transmission ports and the positive sense node of the receive ports.

12. The method of claim 8, wherein the method includes adjusting the compensation impedances such that a first ratio of the compensation impedances to first impedances coupled to the receive ports is approximately equal to a second ratio of second impedances coupled to the transmit ports to a combination of electrode impedances to the sample under test and sample impedance.

13. The method of claim 8, wherein the method includes adjusting the compensation impedances by adjusting a programmable resistance and a programmable capacitance under control of a processing device.

14. The method of claim 13, wherein adjusting the compensation impedances includes iteratively adjusting the compensation impedances to minimize the carrier signal at the receive ports of the impedance measurement circuit.

15. The method of claim 8, wherein the method includes:
outputting an in-phase signal and a quadrature phase signal; and
processing the in-phase signal.

16. A device having an impedance measurement circuit, the device comprising:
a means to transmit a carrier signal to a sample under test;
a means to receive sidebands of the carrier signal in response to modulation of the carrier signal from the sample under test; and
a means to suppress the carrier signal in the reception of the sidebands, with the means to suppress the carrier signal coupled between the means to transmit the carrier signal and the means to receive the sidebands of the carrier signal;
a means to mix the carrier signal with a version of the received sidebands of the carrier signal; and
a means to process information to:
generate a value of impedance of the sample under test in a non-modulated state from impedance information about the means to suppress the carrier signal; and
combine the value of the impedance of the sample under test in the non-modulated state with a measured impedance of the sample under test from the received sidebands.

17. The device of claim 16, wherein the means to transmit the carrier signal includes a positive drive node to transmit a positive drive signal to a first electrode coupled to the sample under test and a negative drive node to transmit a negative drive signal to a second electrode coupled to the sample under test opposite the coupling of the first electrode to the sample under test.

18. The device of claim 17, wherein the means to suppress the carrier signal includes:
a first compensation impedance coupled between the positive drive node and a negative sense node of the means to receive sidebands of the carrier signal; and
a second compensation impedance coupled between the negative drive node and a positive sense node of the means to receive sidebands of the carrier signal.

19. The device of claim 16, wherein the means to suppress the carrier signal includes a means to adjust the means to suppress the carrier signal.

* * * * *